United States Patent [19]

Blanch et al.

[11] Patent Number: 4,817,416
[45] Date of Patent: Apr. 4, 1989

[54] ON-LINE RHEOLOGICAL MEASUREMENTS

[75] Inventors: John F. Blanch, Mantoloking; Ronald F. Garritano, Flemington, both of N.J.; William D. Richards, Scotia; Joseph C. Golba, Jr., Ballston Spa, both of N.Y.

[73] Assignee: Rheometrics, Inc., Piscataway, N.J.

[21] Appl. No.: 206,035

[22] Filed: Jun. 13, 1988

[51] Int. Cl.$^4$ .......................................... G01N 11/08
[52] U.S. Cl. ...................................................... 73/55
[58] Field of Search ...................... 73/55, 56; 137/2, 4, 137/92

[56] References Cited

U.S. PATENT DOCUMENTS

| | | | |
|---|---|---|---|
| 3,138,950 | 6/1954 | Welty et al. | 73/55 |
| 3,559,464 | 2/1971 | Foust et al. | 73/55 |
| 3,938,369 | 2/1976 | de Bok | 73/55 |
| 4,213,747 | 7/1980 | Friedrich | 73/55 X |

FOREIGN PATENT DOCUMENTS

| | | | |
|---|---|---|---|
| 1168123 | 4/1964 | Fed. Rep. of Germany | 73/55 |
| 26837 | 9/1970 | Japan | 73/55 |

Primary Examiner—Stewart J. Levy
Assistant Examiner—Joseph W. Roskos
Attorney, Agent, or Firm—Samuelson & Jacob

[57] ABSTRACT

On-line rheological measurements are made utilizing a rheometer of the type in which a first metering pump delivers diverted melt from a process main stream to a capillary passage and a second metering pump returns the diverted melt from the capillary passage to the process main stream and the viscosity of the diverted melt is measured by controlling the rate of flow of the melt to maintain constant the pressure drop between spaced apart locations along the capillary passage and measuring the temperature of the melt in the capillary passage. The measurements may be made while controlling the speed of the second metering pump independent of the speed of the first metering pump to maintain the pressure at the exit of the capillary passage essentially constant. The capillary passage is placed in close proximity to the process main stream for maintaining a relatively short residence time during which the diverted melt resides outside the process main stream so as to attain a relatively quick response to changes in the measured viscosity. The rheometer includes a relatively thin plate interposed between first and second blocks, the plate including a slot establishing a chamber between the first and second blocks for providing the capillary passage.

18 Claims, 4 Drawing Sheets

ON-LINE RHEOLOGICAL MEASUREMENTS

The present invention relates generally to the measurement of rheological characteristics of melted materials and pertains, more specifically, to the on-line measurement of such characteristics as the viscosity of polymer melts for purposes of control of manufacturing processes involving molten plastics.

Rheological testing equipment has been available for a very long time in conducting laboratory measurements of certain important characteristics of polymer melts used in various manufacturing processes. Thus, such properties as viscosity and melt flow index are being measured in the laboratory with increasing accuracy. More recently, efforts have been directed toward the measurement of these characteristics on-line, during the manufacturing process itself, in order to provide constant, closer control over the quality of the melt utilized in the process. On-line measurement requires equipment which not only is relatively easy to use and maintain, but which is rugged enough to withstand the operating conditions to which the equipment will be exposed. In order to be effective, the equipment must be responsive, and must avoid disturbing the manufacturing process being monitored.

Among the more successful on-line rheometers available currently are capillary rheometers which divert a portion of the polymer melt from the main stream of molten plastic, conduct measurements on the diverted melt, and then discard the diverted melt. Discarding of the diverted melt is wasteful and proper disposal of the discarded melt often presents a problem which must be dealt with in the manufacturing plant. More recently, rheometers have been developed in which the diverted melt is returned to the main stream, thereby eliminating waste and disposal problems. These rheometers usually employ a first metering pump, such as a gear pump, to feed a capillary passage with a controlled flow of diverted melt, and a second metering pump to return the diverted melt to the main stream. Pressure drop along the capillary passage is measured and the temperature of the diverted melt is closely controlled with an independent heating or cooling arrangement in order to measure viscosity, as a function of the measure of the pressure drop, to gain the information necessary to control the process. The present invention constitutes an improvement in on-line capillary rheometers and in the techniques which utilize apparatus of the type in which melt is diverted to a rheometer and the diverted melt is returned to the main stream and extends the capability of such on-line rheometers to enable effective use in connection with the control of processes where measurements must be conducted quickly and response time must be held to a minimum, such as processes in which polymers are blended, alloyed or reacted. More specifically, the present invention has several objectives and provides a number of advantages, some of which are summarized as follows: Enables truly on-line measurements for attaining quicker response and more accurate control of manufacturing processes involving polymer melts; allows on-line measurements without the necessity for controlling the temperature of the diverted polymer melt, thereby enabling measurements to be made in close proximity to the main stream of polymer melt for decreased residence time, increased accuracy and quicker response; permits the conduct of on-line measurements with a minimal intrusion into the process being monitored; permits increased versatility in the nature and extent of the information derived from on-line measurements of polymer melts, as well as increased accuracy in the information itself; enables ease of installation and use in connection with current manufacturing equipment and techniques; allows ready adaptation for use in connection with a wide variety of materials and operating conditions; provides a convenient station for additional sensing and observation devices available for monitoring the quality of the polymer melt; facilitates cleaning and general maintenance, as well as replacement of component parts either for repair or adaptation to specific materials and operating conditions; and provides a simple and rugged construction for economical manufacture and reliable long-term service.

The above objects and advantages, as well as further objects and advantages, are attained by the present invention, which may be described briefly as an improvement whereby on-line rheological measurements are made in a process melt so as to provide process control information based upon the viscosity of the process melt, utilizing a rheometer of the type in which a first metering pump delivers diverted melt from a process main stream to the entrance of a capillary passage and a second metering pump returns the diverted melt from the exit of the capillary passage to the process main stream and the diverted melt is subjected to a pressure drop between spaced apart locations along the capillary passage between the entrance and the exit, by measuring the viscosity of the diverted melt by controlling the rate of flow of the melt through the capillary passage to maintain essentially constant the pressure drop in the diverted melt between the spaced apart locations and measuring the actual temperature of the diverted melt in the capillary passage so as to provide the process control information based upon the measured viscosity of the diverted melt corrected to a known standard by the measured temperature of the diverted melt. The speed of the second metering pump may be controlled independent of the speed of the first metering pump so as to maintain the pressure at the exit essentially constant while the diverted melt is subjected to the pressure drop in the capillary passage. The capillary passage is placed in close proximity to the process main stream by a mounting plate which includes a relatively short first conduit between the process main stream and the entrance to the capillary passage, and a relatively short second conduit between the exit of the capillary passage and the process, main stream for maintaining a relatively short residence time during which the diverted melt resides outside the process main stream so as to attain a relatively quick response to changes in the measured viscosity. The rheometer includes a first block, a second block juxtaposed with the first block, and a relatively thin plate interposed between the first block and the second block, the plate including a slot providing a chamber between the first and second blocks, the chamber extending along a direction from the entrance toward the exit for providing the capillary passage between the entrance and the exit.

The invention will be understood more fully, while still further objects and advantages will become apparent, in the following detailed description of preferred embodiments of the invention illustrated in the accompanying drawing, in which.

Figure 1:
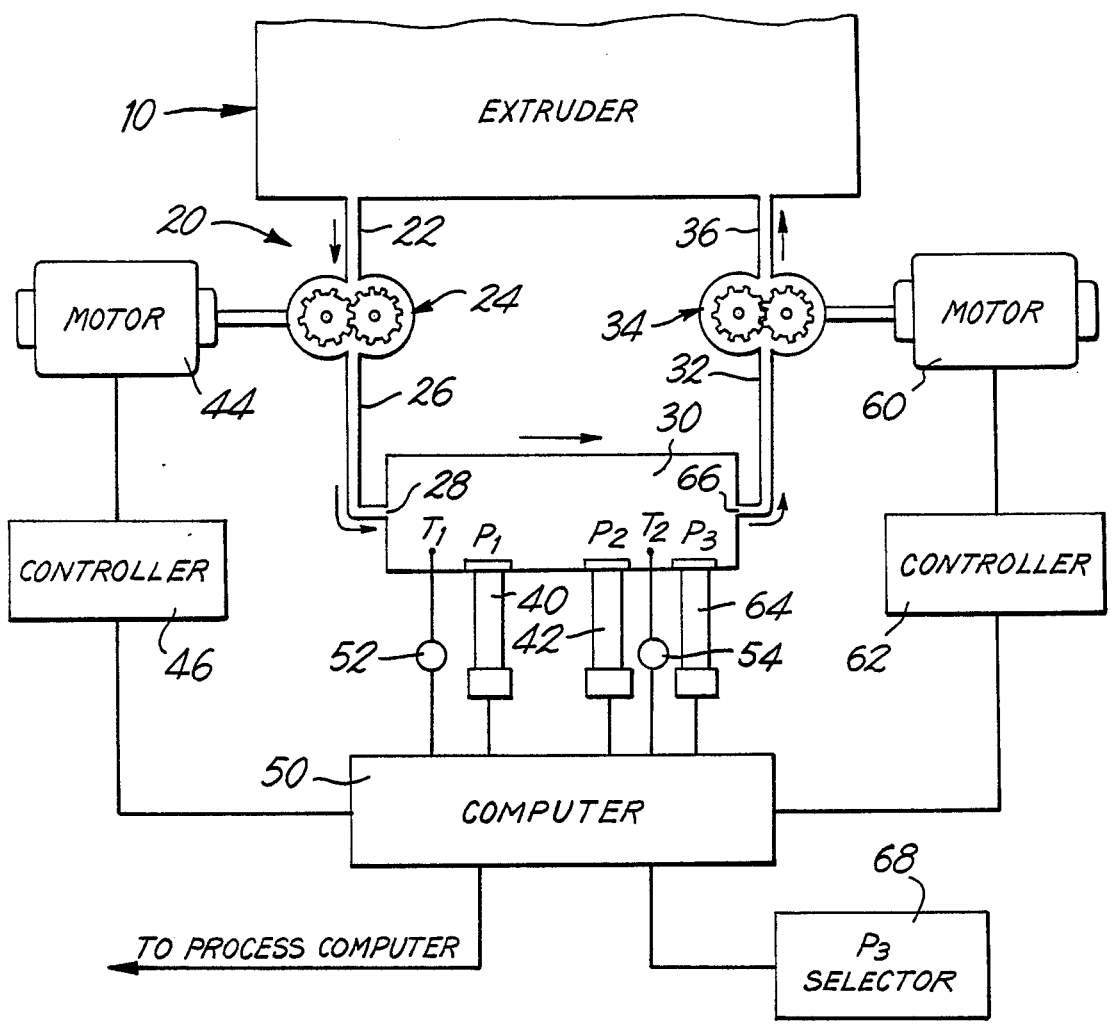
FIG. 1 is a schematic diagram of an on-line system employing the improvement of the present invention.

Referring now to the drawing, and especially to FIG. 1 thereof, a plasticating extruder is shown schematically at 10. Extruder 10 is in use, generating melted polymer for the continuous manufacture of items constructed of plastic material. In order to assure that the quality of the extrudate meets the requirements of the manufacturing process, a control system is utilized in connection with the operation of the extruder to monitor certain characteristics of the polymer melt and to operate the extruder in the manner necessary to attain the desired quality in the extrudate. An on-line rheometer 20, constructed in accordance with the present invention, is a part of that control system.

A portion of the polymer melt in the extruder 10 is diverted from the main stream in the extruder to the rheometer 20 through an inlet conduit 22 and is advanced by a first metering pump 24 through an entrance conduit 26 to the entrance 28 to a capillary passage 30 of selected configuration and dimensions. The diverted polymer melt traverses the capillary passage 30 and then leaves the capillary passage 30 via an exit conduit 32. A second metering pump 34 advances the diverted polymer melt through an outlet conduit 36 which communicates with the extruder 10 so that the diverted polymer melt is returned to the main stream of polymer melt in the extruder 10. A first pressure-responsive transducer 40 is placed at a location adjacent the entrance 28 and provides information indicative of the pressure $P_1$ in the polymer melt at that location in the capillary passage 30. A second pressure-responsive transducer 42 is placed at a second location spaced downstream from the first location and provides information indicative of the pressure $P_2$ at the second location in the capillary passage 30. The rate of flow of the polymer melt in the capillary passage 30 is governed by the speed of the first metering pump 24 and that speed is determined by the speed of the motor 44 which drives the metering pump 24. The speed of motor 44 is controlled by a controller 46 which itself is connected to a computer 50. Temperature sensors 52 and 54 provide information to computer 50 indicative of the temperature ($T_1$ and $T_2$) of the polymer melt adjacent each of the locations of the pressure-responsive transducers 40 and 42.

In currently available rheometers of the type described, viscosity is calculated from the measured pressure drop ($P_1-P_2$) along the capillary passage 30 and the rate of flow of the polymer melt in the capillary passage 30, while the temperature of the polymer melt is maintained at a constant value. Thus, temperature sensors, corresponding to temperature sensors 52 and 54, would be used to provide temperature information to operate a heating or cooling arrangement which would maintain the desired constant temperature in the polymer melt being subjected to stress in a capillary passage corresponding to capillary passage 30, the measure of the stress then being available in terms of the pressure drop (corresponding to $P_1-P_2$) indicated by the pressure-responsive transducers similar to pressure-responsive transducers 40 and 42. It has been found, however, that the necessity for maintaining a constant, selected temperature in the polymer melt traversing the capillary passage requires that the rheometer itself be located relatively remote from the main stream in the extruder, or other process apparatus, in order to avoid the effects of high temperatures and temperature fluctuations in the vicinity of the process apparatus on the temperature of the polymer melt in the capillary passage of the rheometer. Moreover, a finite amount of time is required to bring the temperature of the diverted polymer melt to the selected constant temperature required for the measurements to be performed as the polymer melt traverses the capillary passage. Accordingly, the residence time during which the diverted polymer melt is outside the main stream is relatively high and the response time of the control system which utilizes such a rheometer is concomitantly high.

The present invention reduces residence time and decreases response time, thereby enabling more truly on-line operation, by eliminating the requirement for control of the temperature of the diverted polymer melt, allowing rheometer 20 to be placed in close proximity to extruder 10, or other process apparatus, for a reduction in residence time, during which the diverted polymer melt is outside the main stream, and a concomitant reduction in response time in the control system. Thus, in the present invention, the pressure drop $P_1-P_2$ is maintained constant by controlling the speed of both the first and the second metering pumps 24 and 34. The speed of the first metering pump 24 then provides a measure of the rate of flow of the polymer melt traversing the capillary passage 30, which rate of flow is an indication of the viscosity of the polymer melt. Since the speed of the first metering pump 24 is known with precision, the viscosity is determined with a high degree of accuracy. Since the temperature dependence of polymer materials at constant stress is well known, the maintenance of a constant stress on the polymer melt in the capillary passage 30, that is, the maintenance of a constant pressure drop $P_1-P_2$, enables the temperature information, as determined by $T_1$ and $T_2$ (preferably by averaging $T_1$ and $T_2$), to be utilized to relate the measurements to a known standard so that it is not necessary to control the temperature of the diverted polymer melt, but merely to measure the temperature and then correct the measured viscosity information, in accordance with the measured temperature, to derive the desired control information. In this manner, viscosity measurements are enabled independent of the temperature of the diverted polymer melt. The information pertaining to pressure drop ($P_1-P_2$), rate of flow and temperature ($T_1$ and $T_2$) is directed to computer 50. Computer 50 then provides control information to a process computer which may be used in connection with the control of the operation of the extruder 10.

In order to maintain accuracy in the determination of viscosity, utilizing the above scheme, it is necessary to assure that the pressure drop ($P_1-P_2$) is solely a result of the traverse of the capillary passage 30 by the polymer melt, and that the measured pressures are not affected by any irregularities in the operation of the various components of the rheometer 20. In currently available rheometers of the type described, the metering pumps usually are driven by a common motor and drive and the accuracy of the mechanical components is relied upon to maintain the same flow rate through both metering pumps so that the measured pressures within the capillary passage are unaffected by any variation in flow rate between the two metering pumps. However, it has been observed that unavoidable differences in the operating characteristics of the metering pumps, though small, will cause variations in the measured pressures significant enough to have a deleterious effect upon the accuracy of the control of the extruder. Accordingly, rheometer 20 includes means for driving the second metering pump 34 independent of the first metering pump 24, the means being illustrated in the form of a second motor 60 controlled by a second controller 62 connected to computer 50. A third pressure-responsive transducer 64 is located adjacent exit 66 from the capillary passage 30 and provides information indicative of the pressure $P_3$ at the exit. The information provided by the third pressure-responsive transducer 64 is utilized by the computer 50 to operate the controller 62 so that the motor 60 actuates the second metering pump 34 at the speed necessary to maintain the pressure $P_3$ constant. By maintaining the exit pressure $P_3$ constant, the pressure drop $P_1-P_2$ is related solely to the characteristics of the polymer melt traversing the capillary passage 30 and does not include any effects introduced by inaccuracies in the mechanical components of the rheometer 20. Hence, the information provided by computer 50 is related solely to the characteristics of the polymer melt for accurate control of the process being carried out in the extruder.

The operation of the second metering pump 34 independent of the first metering pump 24 enables the accomplishment of further significant measurements. Thus, in response to selected input into the computer 50, by means of a selector 68, the exit pressure $P_3$ can be changed to any selected constant pressure enabling the measurement of the viscosity of the polymer melt at different pressures, thereby enabling an evaluation of the response of viscosity to pressure. These measurements provide additional information enabling enhanced control of the quality of the extrudate produced by the extruder 10.

Figure 2:
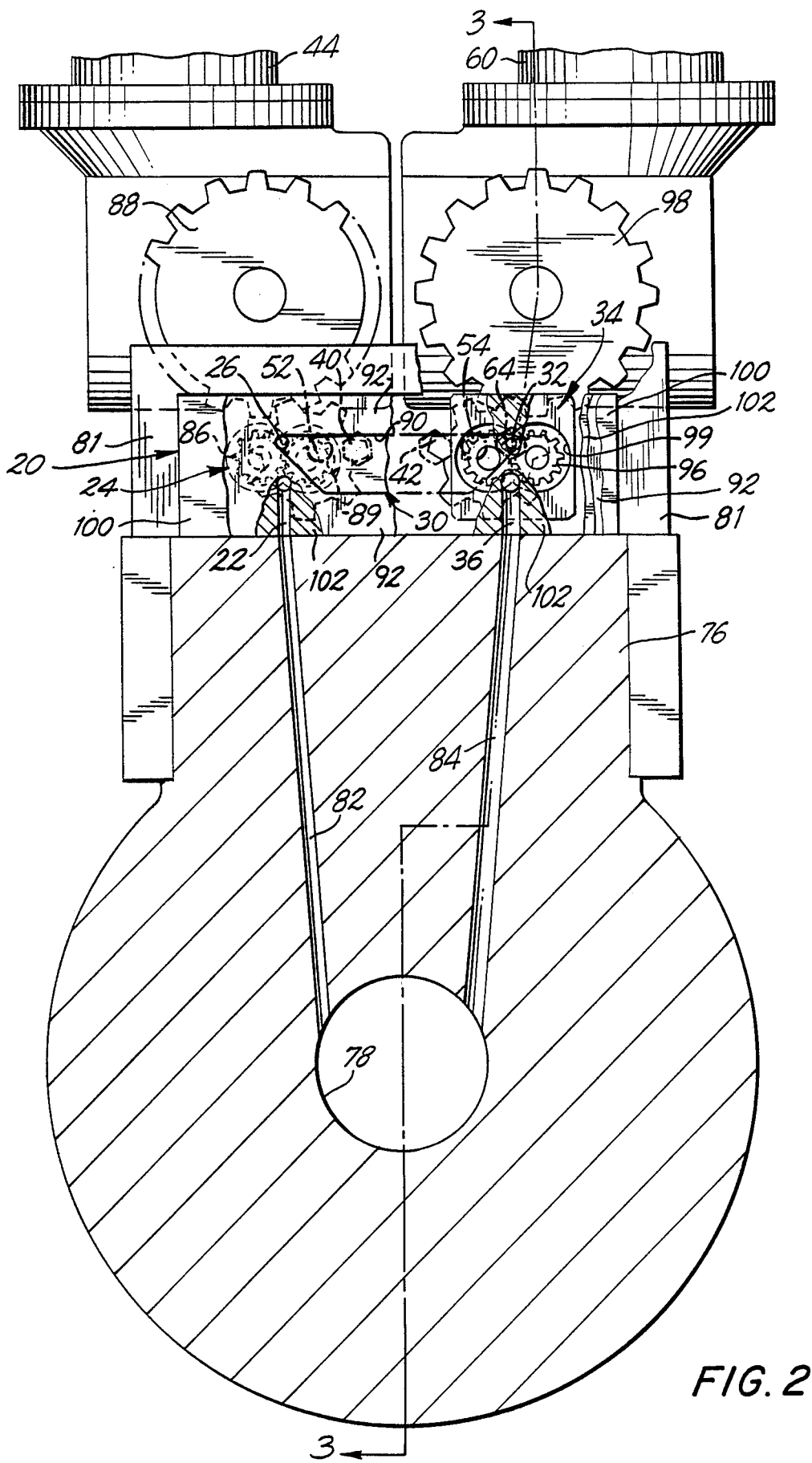
FIG. 2 is a transverse cross-sectional view of an apparatus constructed in accordance with the invention installed in a plasticating extruder.
Figure 3:
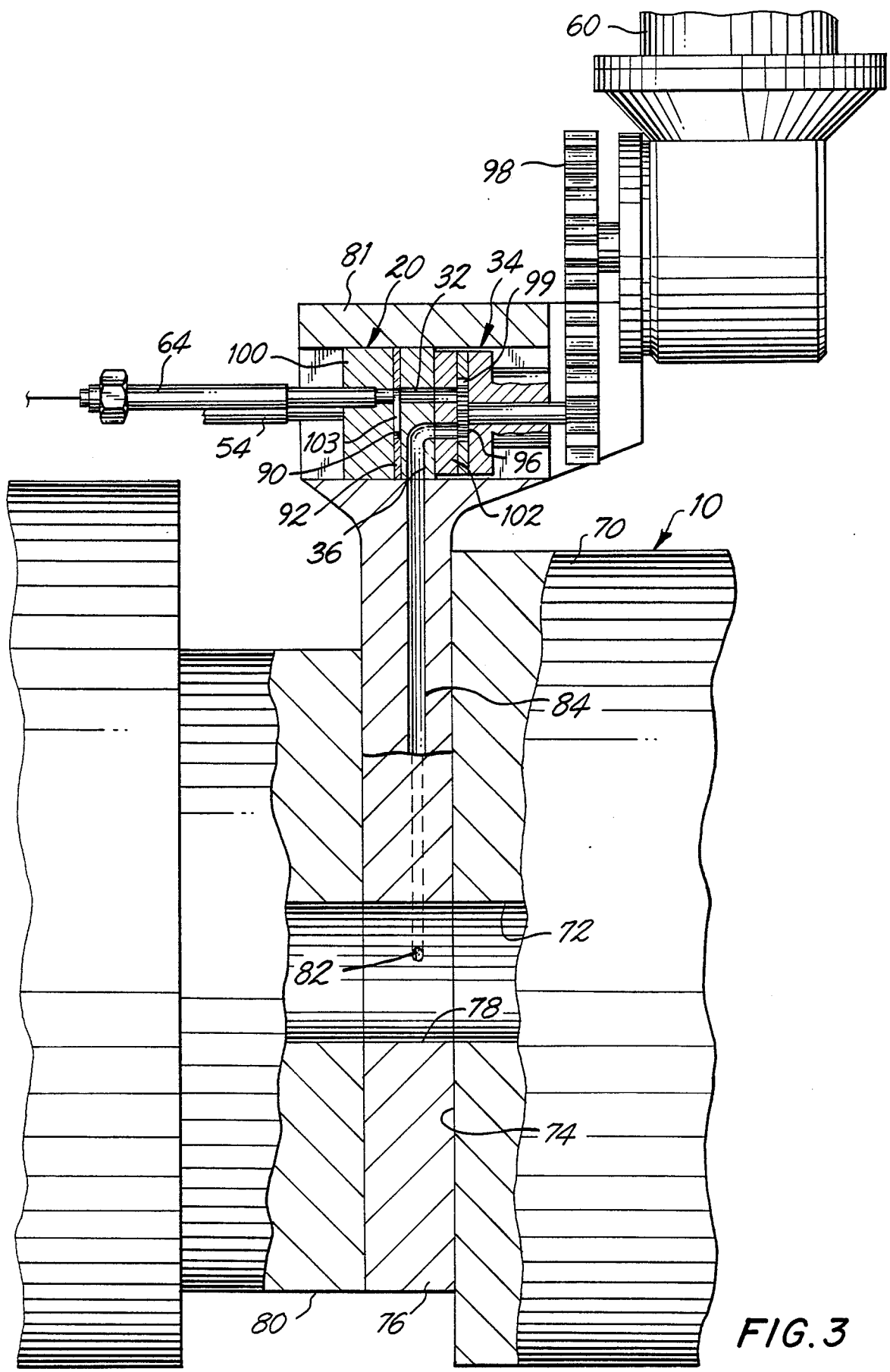
FIG. 3 is a cross-sectional view taken along line 3—3 of FIG. 2.

Turning now to FIGS. 2 and 3, there is illustrated a typical installation in which a rheometer 20 is mounted upon an extruder 10 for on-line operation. Extruder 10 has a barrel 70 which includes an outlet bore 72 at the output end 74 of the extruder 10. A mounting plate 76 is affixed to the end 74 of the barrel 70 and has an aperture 78 which matches the outlet bore 72 of the extruder 10. A further orifice plate 80 is placed downstream of the mounting plate 76. Rheometer 20 is secured to the mounting plate 76 by means of a bracket 81 which is integral with the mounting plate 76 so as to be in very close proximity to the main stream of polymer melt passing from the extruder 10, through the outlet bore 72. An inlet passage 82 in the mounting plate 76 communicates with the aperture 78 and provides a relatively short conduit to the inlet conduit 22 of the rheometer 20. An outlet passage 84 in the mounting plate 76 also communicates with the aperture 78 and provides a relatively short conduit from the outlet conduit 36 of the rheometer 20 back to the aperture 78. A portion of the polymer melt is diverted from the main stream in the outlet bore 72 and the aperture 78 to the inlet passage 82 and is conducted to the inlet conduit 22 of the rheometer 20. The first metering pump 24 is in the form of a gear pump having a pair of gear-type impellers 86 (also see FIG. 4) coupled to the first motor 44 through a drive train 88 for rotation in a pump chamber 89. Capillary passage 30 is in the form of a slot 90 in a capillary plate 92 and the pump chamber 89 communicates with the slot 90 through entrance conduit 26 to deliver the diverted polymer melt from the inlet conduit 22 to the capillary passage 30. The diverted polymer melt traverses the capillary passage 30 and is delivered to the second metering pump 34 via the exit conduit 32. Second metering pump 34 also is in the form of a gear pump having a pair of gear-type impellers 96 coupled to the second motor 60 through a drive train 98 for rotation in a pump chamber 99, independent of the rotation of the impellers 86 of the first metering pump 24. The outlet conduit 36 communicates with the pump chamber 99 and enables return of the diverted polymer melt to the main stream in the aperture 78. Thus, it can be seen that the rheometer 20 is placed in close proximity with the main stream of polymer melt for true on-line operation with a minimal intrusion into the manufacturing process, while enabling simplified installation for adapting the rheometer 20 for use in connection with conventional extruders. The close proximity of the rheometer 20 to the main stream of polymer melt assures that the residence time during which the diverted polymer melt resides in the rheometer, and outside the process main stream, is maintained at a minimum and the control system is able to respond relatively quickly to any changes in the viscosity of the polymer melt. The ability to accomplish the desired measurements without the necessity for controlling the temperature of the diverted polymer melt, as described above, enables the close proximity of the rheometer 20 to the main stream with concomitant low residence time and quick response. In addition, the rheometer is more responsive since it is not necessary to change the temperature of the diverted polymer melt for the purpose of accomplishing an accurate viscosity measurement. All that is necessary is a measurement of the actual temperature of the diverted polymer melt while the polymer melt is under constant stress in the capillary passage.

Figure 4:
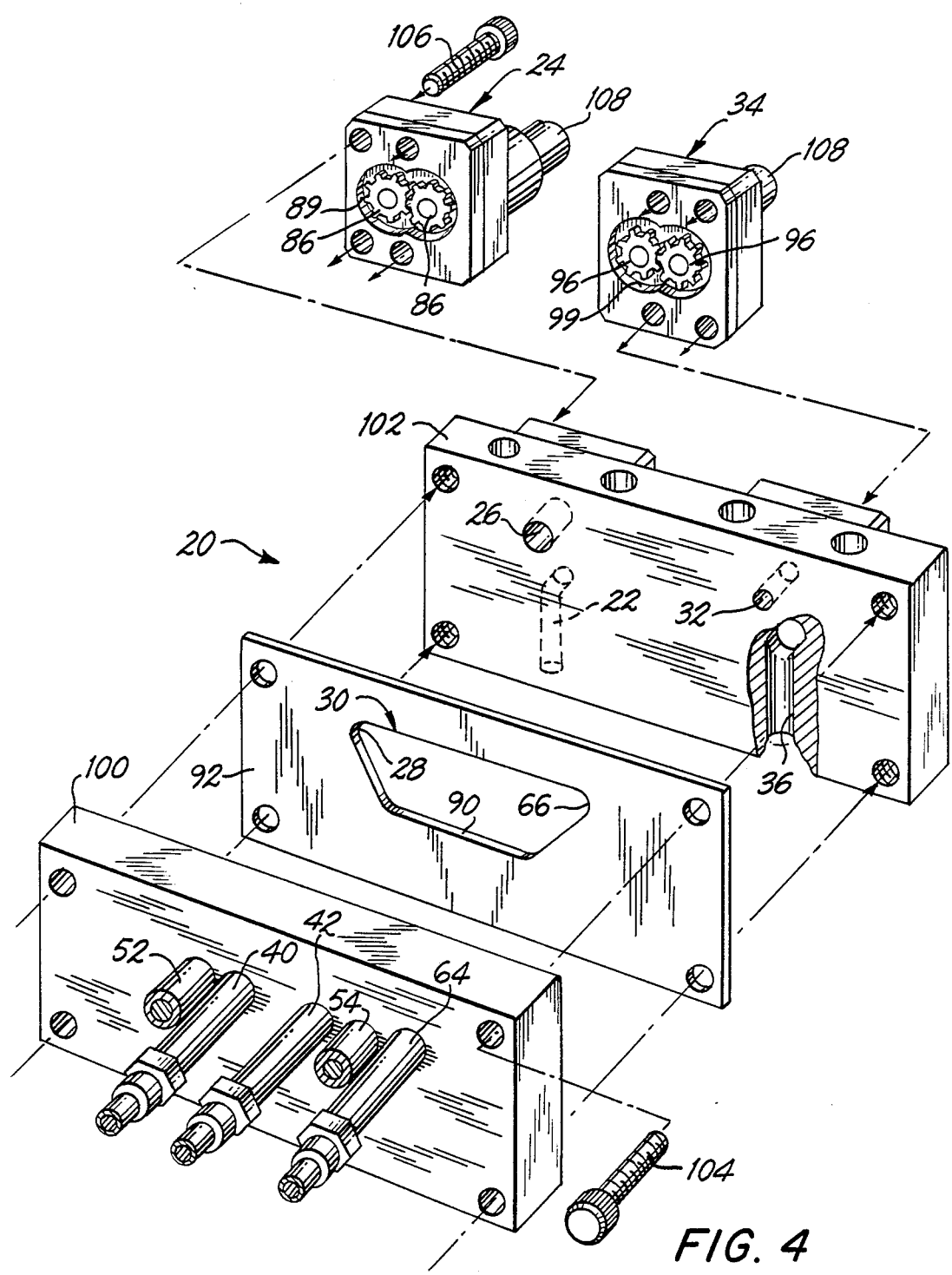
FIG. 4 is an exploded perspective view of portions of the apparatus.

As best seen in FIG. 4, as well as in FIGS. 2 and 3, rheometer 20 preferably is constructed of assembled component parts which include a first block 100 and a second block 102 between which blocks 100 and 102 is interposed the capillary plate 92 such that the slot 90, when placed between the blocks 100 and 102, establishes a chamber 103 (see FIG. 3) which provides the capillary passage 30. The blocks 100 and 102 and the capillary plate 92 are secured together, as with threaded fasteners 104, to establish an integral unit which may be dismantled at will. The metering pumps 24 and 34 likewise are secured to the second block 102, by means of threaded fasteners 106, each metering pump having a drive shaft 108 for coupling the impellers of the pump to the respective drive train. The second block 102 also includes the inlet conduit 22, the entrance conduit 26, the exit conduit 32 and the outlet conduit 36. The first block 100 carries the pressure-responsive transducers 40, 42 and 64, and the temperature sensors 52 and 54.

The capillary plate 92 is relatively thin and the configuration and dimensions of the capillary slot 90 are chosen to provide a capillary passage 30 of corresponding configuration and dimensions appropriate for enabling the desired measurements to be made in the particular polymer involved in the process being monitored. The various conduits in the second block 102 and the several transducers and sensors in the first block 100 are placed so as to be located appropriately relative to the slot 90. Capillary plate 92 is readily accessible for ease of cleaning and maintenance, and is replaced easily for adapting the rheometer 20 for use with any one of a variety of materials and operating conditions. For example, any one of a series of plates 92, each having a slot 90 of a different configuration and different dimensions, may be selected for a particular installation. The location of the rheometer 20 renders the rheometer easily available for repair or replacement. That same location places the rheometer 20 within easy reach for connection and disconnection with the computer 50, and for adapting the rheometer for other tasks involving the examination of the polymer melt such as, for example, the visual observation of the polymer melt for unwanted inclusions, as described in U.S. Pat. No. 4,529,306.

It will be seen that the above-described apparatus and procedure enables truly on-line measurements for quicker response and more accurate control of manufacturing processes involving polymer melts; allows on-line measurements without the necessity for controlling the temperature of the diverted polymer melt, thereby enabling measurements to be made in close proximity to the main stream of polymer melt for decreased residence time, increased accuracy and quicker response; attains on-line measurements with a minimal intrusion into the process being monitored; permits increased versatility in the nature and extent of the information derived from on-line measurements of polymer melts, as well as increased accuracy in the information itself; allows ease of installation and use in connection with current manufacturing equipment and techniques; is adapted readily for use in connection with a wide variety of materials and operating conditions; provides a convenient station for additional sensing and observation devices available for monitoring the quality of the polymer melt; facilitates cleaning and general maintenance, as well as replacement of component parts either for repair or adaptation to different materials and specific operating conditions; and allows a simple and rugged construction for economical manufacture and reliable long-term service.

It is to be understood that the above detailed description of embodiments of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. In the method for conducting an on-line rheological measurement in a process melt so as to provide process control information based upon the viscosity of the process melt, utilizing a rheometer of the type in which a first metering pump delivers diverted melt from a process main stream to the entrance of a capillary passage and a second metering pump returns the diverted melt from the exit of the capillary passage to the process main stream and the diverted melt is subjected to a pressure drop between spaced apart locations along the capillary passage between the entrance and the exit, the improvement comprising: measuring the viscosity of the diverted melt by controlling the rate of flow of the melt through the capillary passage to maintain essentially constant the pressure drop in the diverted melt between the spaced apart locations and measuring the actual temperature of the diverted melt in the capillary passage so as to provide the process control information based upon the measured viscosity of the diverted melt corrected to a known standard by the measured temperature of the diverted melt.

2. The invention of claim 1 including the step of controlling the speed of the second metering pump independent of the speed of the first metering pump so as to maintain the pressure at the exit essentially constant.

3. The invention of claim 1 including the steps of controlling the speed of the second metering pump independent of the speed of the first metering pump to select the pressure at the exit, selecting the pressure at the exit and measuring the viscosity of the diverted melt at a plurality of different selected constant pressures at the exit.

4. In apparatus for conducting an on-line rheological measurement in a process melt so as to provide process control information based upon the viscosity of the process melt, utilizing a rheometer of the type in which a first metering pump delivers diverted melt from a process main stream to the entrance of a capillary passage and a second metering pump returns the diverted melt from the exit of the capillary passage to the process main stream and the diverted melt is subjected to a pressure drop between spaced apart locations along the capillary passage between the entrance and the exit, the improvement comprising: means for measuring the viscosity of the diverted melt by controlling the rate of flow of the melt through the capillary passage to maintain essentially constant the pressure drop in the diverted melt between the spaced apart locations and measuring the actual temperature of the diverted melt in the capillary passage so as to provide the process control information based upon the measured viscosity of the diverted melt corrected to a known standard by the measured temperature of the diverted melt.

5. The invention of claim 4 including means for controlling the speed of the second metering pump independent of the speed of the first metering pump so as to maintain the pressure at the exit essentially constant.

6. The invention of claim 4 including means for controlling the speed of the second metering pump independent of the speed of the first metering pump to select the pressure at the exit, and means for selecting the pressure at the exit to enable the viscosity of the diverted melt to be measured at a plurality of different selected pressures at the exit.

7. The invention of claim 4 including mounting means for placing the capillary passage in close proximity to the process main stream, the mounting means including a relatively short first conduit between the process main stream and the entrance to the capillary passage, and a relatively short second conduit between the exit of the capillary passage and the process main stream for maintaining a relatively short residence time during which the diverted melt resides outside the process main stream so as to attain a relatively quick response to changes in the measured viscosity.

8. The invention of claim 4 wherein the rheometer includes a first block, a second block juxtaposed with the first block, and a relatively thin plate interposed between the first block and the second block, the plate including a slot providing a chamber between the first and second blocks, the chamber extending along a direction from the entrance toward the exit for providing the capillary passage between the entrance and the exit.

9. The invention of claim 8 including means enabling selective release of the plate from between the blocks for selective maintenance or replacement.

10. In an on-line rheometer of the type in which a first metering pump delivers diverted melt from a process main stream to the entrance of a capillary passage and a second metering pump returns the diverted melt from the exit of the capillary passage to the process main stream and the viscosity of the diverted melt is measured by subjecting the diverted melt to a pressure drop between spaced apart locations along the capillary passage between the entrance and the exit, the improvement comprising: mounting means for placing the capillary passage in close proximity to the process main stream, the mounting means including a relatively short first conduit between the process main stream and the entrance to the capillary passage, and a relatively short second conduit between the exit of the capillary passage and the process main stream for maintaining a relatively short residence time during which the diverted melt resides outside the process main stream and attaining a relatively quick response to changes in the measured viscosity.

11. The invention of claim 10 wherein the rheometer includes a first block, a second block juxtaposed with the first block, and a relatively thin plate interposed between the first block and the second block, the plate including a slot providing a chamber between the first and second blocks, the chamber extending along a direction from the entrance toward the exit for providing the capillary passage between the entrance and the exit.

12. The invention of claim 11 including means enabling selective release of the plate from between the blocks for selective maintenance or replacement.

13. In an on-line rheometer of the type in which a first metering pump delivers diverted melt from a process main stream to the entrance of a capillary passage and a second metering pump returns the diverted melt from the exit of the capillary passage to the process main stream and the viscosity of the diverted melt is measured by subjecting the diverted melt to a pressure drop between spaced apart locations along the capillary passage between the entrance and the exit, the improvement wherein the rheometer includes a first block, a second block juxtaposed with the first block, and a relatively thin plate interposed between the first block and the second block, the plate including a slot providing a chamber between the first and second blocks, the chamber extending along a direction from the entrance toward the exit for providing the capillary passage between the entrance and the exit.

14. The invention of claim 13 including means enabling selective release of the plate from between the blocks for selective maintenance or replacement.

15. In the method for conducting an on-line rheological measurement utilizing a rheometer of the type in which a first metering pump delivers diverted melt from a process main stream to the entrance of a capillary passage and a second metering pump returns the diverted melt from the exit of the capillary passage to the process main stream and the viscosity of the diverted melt is measured by subjecting the diverted melt to a pressure drop between spaced apart locations along the capillary passage between the entrance and the exit, the improvement comprising: controlling the speed of the second metering pump independent of the speed of the first metering pump so as to maintain the pressure at the exit essentially constant while subjecting the diverted melt to the pressure drop between the spaced apart locations along the capillary passage.

16. The invention of claim 15 including the steps of selecting the pressure at the exit and subjecting the diverted melt to the pressure drop between the spaced apart locations along the capillary passage at a plurality of different selected constant pressures at the exit.

17. In an on-line rheometer of the type in which a first metering pump delivers diverted melt from a process main stream to the entrance of a capillary passage and a second metering pump returns the diverted melt from the exit of the capillary passage to the process main stream and the viscosity of the diverted melt is measured by subjecting the diverted melt to a pressure drop between spaced apart locations along the capillary passage between the entrance and the exit, the improvement comprising: means for controlling the speed of the second metering pump independent of the speed of the first metering pump so as to maintain the pressure at the exit essentially constant while subjecting the diverted melt to the pressure drop between the spaced apart locations along the capillary passage.

18. The invention of claim 17 including means for selecting the pressure at the exit such that the diverted melt is subjected to the pressure drop between the spaced apart locations along the capillary passage at a plurality of different selected constant pressures at the exit.

* * * * *